(12) United States Patent
Wittenberger

(10) Patent No.: US 9,333,023 B2
(45) Date of Patent: *May 10, 2016

(54) BALLOON CATHETER WITH DEFORMABLE FLUID DELIVERY CONDUIT

(71) Applicant: Medtronic CryoCath LP, Toronto (CA)

(72) Inventor: Dan Wittenberger, L'ile Bizard (CA)

(73) Assignee: Medtronic CryoCath LP, Toronto, Ontario (CA)

( * ) Notice: Subject to any disclaimer, the term of this patent is extended or adjusted under 35 U.S.C. 154(b) by 0 days.

This patent is subject to a terminal disclaimer.

(21) Appl. No.: 14/549,972

(22) Filed: Nov. 21, 2014

(65) Prior Publication Data

US 2015/0080870 A1  Mar. 19, 2015

Related U.S. Application Data

(62) Division of application No. 12/910,492, filed on Oct. 22, 2010, now Pat. No. 8,911,434.

(51) Int. Cl.
*A61B 18/02* (2006.01)
*A61B 18/00* (2006.01)

(52) U.S. Cl.
CPC ....... *A61B 18/02* (2013.01); *A61B 2018/00214* (2013.01); *A61B 2018/00345* (2013.01); *A61B 2018/00375* (2013.01); *A61B 2018/00577* (2013.01); *A61B 2018/0212* (2013.01); *A61B 2018/0268* (2013.01)

(58) Field of Classification Search
CPC ........ A61B 18/02; A61B 18/04; A61B 18/08; A61B 18/082; A61B 18/10; A61B 18/12; A61B 18/14; A61B 18/1466; A61B 2018/00214; A61B 2018/00345; A61B 2018/00375; A61B 2018/00577; A61B 2018/0212; A61B 2018/0268

USPC ....................................................... 606/21–26
See application file for complete search history.

(56) References Cited

U.S. PATENT DOCUMENTS

| | | | |
|---|---|---|---|
| 5,873,852 | A | 2/1999 | Vigil et al. |
| 6,551,274 | B2 | 4/2003 | Heiner |
| 6,875,209 | B2 | 4/2005 | Zvuloni et al. |
| 6,979,331 | B2 | 12/2005 | Hintringer et al. |
| 7,101,367 | B2 | 9/2006 | Xiao et al. |
| 7,101,368 | B2 | 9/2006 | Lafontaine |
| 7,220,257 | B1 | 5/2007 | Lafontaine |

(Continued)

FOREIGN PATENT DOCUMENTS

| | | |
|---|---|---|
| CN | 1780590 A | 5/2006 |
| CN | 101472531 A | 7/2009 |
| EP | 1356779 B1 | 6/2007 |

OTHER PUBLICATIONS

The State Intellectual Property Office of the People's Republic of China, Oct. 23, 2014 Notice on the First Office Action and Search Report for Application No: 201180050491.5, 9 pages.

*Primary Examiner* — Michael Peffley
*Assistant Examiner* — Khadijeh Vahdat
(74) *Attorney, Agent, or Firm* — Christopher & Weisberg, P.A.

(57) ABSTRACT

A medical device, including an elongate body having a proximal portion and a distal portion; a shaft at least partially disposed within the elongate body; an expandable element at the distal portion of the elongate body; and a fluid delivery conduit defining a deflectable segment movably coupled to the shaft, the deflectable segment being transitionable from a substantially linear configuration to a substantially curvilinear configuration.

18 Claims, 4 Drawing Sheets

(56) References Cited

U.S. PATENT DOCUMENTS

| | | |
|---|---|---|
| 7,500,973 B2 | 3/2009 | Vancelette et al. |
| 2005/0033287 A1 | 2/2005 | Sra |
| 2006/0247611 A1 | 11/2006 | Abboud et al. |
| 2007/0208329 A1 | 9/2007 | Ward et al. |
| 2007/0250050 A1 | 10/2007 | Lafontaine |
| 2008/0215043 A1 | 9/2008 | Abboud et al. |
| 2008/0243111 A1 | 10/2008 | Gammie et al. |
| 2008/0312644 A1 | 12/2008 | Fourkas et al. |
| 2009/0118723 A1 | 5/2009 | Lalonde et al. |
| 2011/0184398 A1 | 7/2011 | Desrochers |

BALLOON CATHETER WITH DEFORMABLE FLUID DELIVERY CONDUIT

CROSS-REFERENCE TO RELATED APPLICATION

This application is related to and claims priority to U.S. Utility patent application Ser. No. 12/910,492, filed Oct. 22, 2010, entitled BALLOON CATHETER WITH DEFORMABLE FLUID DELIVERY CONDUIT, now U.S. Pat. No. 8,911,434 issued Dec. 16, 2014, the entirety of which is incorporated herein by reference.

STATEMENT REGARDING FEDERALLY SPONSORED RESEARCH OR DEVELOPMENT n/a

FIELD OF THE INVENTION

The present invention relates to a method and system for tissue treatment, and in particular, towards systems and methods of use thereof for thermally ablating cardiac tissue.

BACKGROUND OF THE INVENTION

Minimally invasive devices, such as catheters, are often employed for medical procedures, including those involving mapping, ablation, dilation, and the like. In a particular situation, an ablation procedure may involve creating a series of inter-connecting or otherwise substantially continuous lesions in order to electrically isolate tissue believed to be the source of an arrhythmia. During the course of such a procedure, a physician may employ several different catheters having variations in the geometry and/or dimensions of the ablative element in order to produce the desired ablation pattern and/or continuity. Each catheter may have a unique geometry for creating a specific lesion or pattern, with the multiple catheters being sequentially removed and replaced during a designated procedure to create the desired multiple lesions constituting a pattern or continuous segment of treated tissue. In addition, a selected device may have a substantially fixed geometry or dimension for a specific application and as such, may be limited to use in situations where the fixed dimensions of the device are appropriate. However, variations in the dimensions or characteristics of physiological structures may vary from patient to patient, rendering a device with specific dimensions or fixed configuration ineffective and/or difficult to use. As such, multiple devices having a range of varying fixed dimensions may be needed to successfully perform a desired treatment. Exchanging these various devices during a procedure can cause inaccuracies or movement in the placement and location of the distal tip with respect to the tissue to be ablated, and may further add to the time required to perform the desired treatment. These potential inaccuracies and extended duration of the particular procedure, not to mention the risks of complications from repeatedly inserting and retracting devices to and from an incision site, increase the risk to the patient undergoing treatment.

In addition to the inefficiencies and risks associated with using multiple devices to perform a procedure, the efficacy of certain treatment procedures, such as those involving thermal energy transfer, may be limited by poor thermal conductivity between a device and the tissue site. To provide shorter treatment durations and increased efficacy for the particular treatment provided, it is desirable to optimize the heat transfer between the specific tissue to be treated and the cryogenic element or device. In other words, heat transfer from any tissue other than that selected for treatment, such as blood or other body fluids in or passing through the vicinity of the cryogenic element for example, should be minimized or avoided. Such thermal exchange with tissues or fluids other than that targeted for treatment can reduce the thermal exchange with the targeted tissue and also require additional "cooling power" or refrigerant flow in the case of cryogenic cooling in order to complete the desired treatment. Accordingly, heat transfer with any thermal load other than the tissue to be treated should be reduced or prevented.

Accordingly, in light of the above limitations, it would be desirable to provide a medical device in which the particular size, shape, and/or dimensions of the device may be controlled and modified during use to provide ablative patterns or treatment delivery characteristics of various shapes and continuity, without the need for additional catheters or the like having a single geometric orientation that is limited in its ability to provide multiple ablative patterns or treatment characteristics for a specific tissue region. It would also be desirable to provide an apparatus and methods of use thereof having increased heat transfer efficiency during thermal exchange procedures.

SUMMARY OF THE INVENTION

The present invention advantageously provides a medical system and methods of use thereof in which the particular size, shape, and/or dimensions of the components of the system may be controlled and modified during use to provide ablative patterns or treatment delivery characteristics of various shapes and continuity, as well as having increased heat transfer efficiency during thermal exchange procedures. In particular, a medical device is disclosed, including an elongate body having a proximal portion and a distal portion; a shaft at least partially disposed within the elongate body; an expandable element at the distal portion of the elongate body; and a fluid delivery conduit defining a deflectable segment movably coupled to the shaft, the deflectable segment being transitionable from a substantially linear configuration to a substantially curvilinear configuration. The fluid delivery conduit may define at least one helical opening, the device may include a cryogenic coolant source in fluid communication with the fluid delivery conduit, and the shaft may be movable with respect to the elongate body and define a lumen therein for passage of a guide wire. The elongate body may define an exhaust lumen in fluid communication with an interior of the expandable element, and the deflectable segment may define a proximal end and a distal end, the proximal end being slidably and rotatably coupled to the shaft, where the distal end is immovably fixed to the shaft. The device may also include a first actuator coupled to the deflectable segment to adjust a longitudinal position of at least a portion of the deflectable segment and a second actuator coupled to the deflectable segment to adjust a rotational position of at least a portion of the deflectable segment.

A method of thermally treating tissue is disclosed, including positioning an expandable element of a medical device adjacent to the tissue; delivering a fluid into an interior of the expandable element with a fluid delivery conduit to expand the expandable element, the fluid delivery conduit being in a first geometric configuration; thermally treating a first region of the tissue with the expandable element; transitioning the fluid delivery conduit from the first geometric configuration into a second geometric configuration; and thermally treating a second region of the tissue with the expandable element. The first geometric configuration may be substantially linear and the second geometric configuration may be curvilinear. The first region may have a shape different from a shape of the second region, where the shape of the first region is substantially circular. Transitioning the fluid delivery conduit from the first geometric configuration into a second geometric configuration may include rotating at least a portion of the fluid delivery conduit about a guide wire lumen of the medical device and/or longitudinally sliding at least a portion of the fluid delivery conduit along a guide wire lumen of the medical device. Delivering a fluid may include extending a portion of the fluid delivery conduit defining at least on helical opening to increase a rate of fluid flow into the expandable element and/or compressing a portion of the fluid delivery conduit defining at least one helical opening to decrease a rate of fluid flow into the expandable element. Thermally treating the tissue may include ablating at least a portion of the tissue, and the tissue includes an ostium of a pulmonary vein, and the method may also include terminating coolant dispersion into the interior cavity; transitioning the fluid delivery conduit from the second geometric configuration to the first configuration; and removing the expandable element from the tissue.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION OF THE INVENTION

Figure 1:
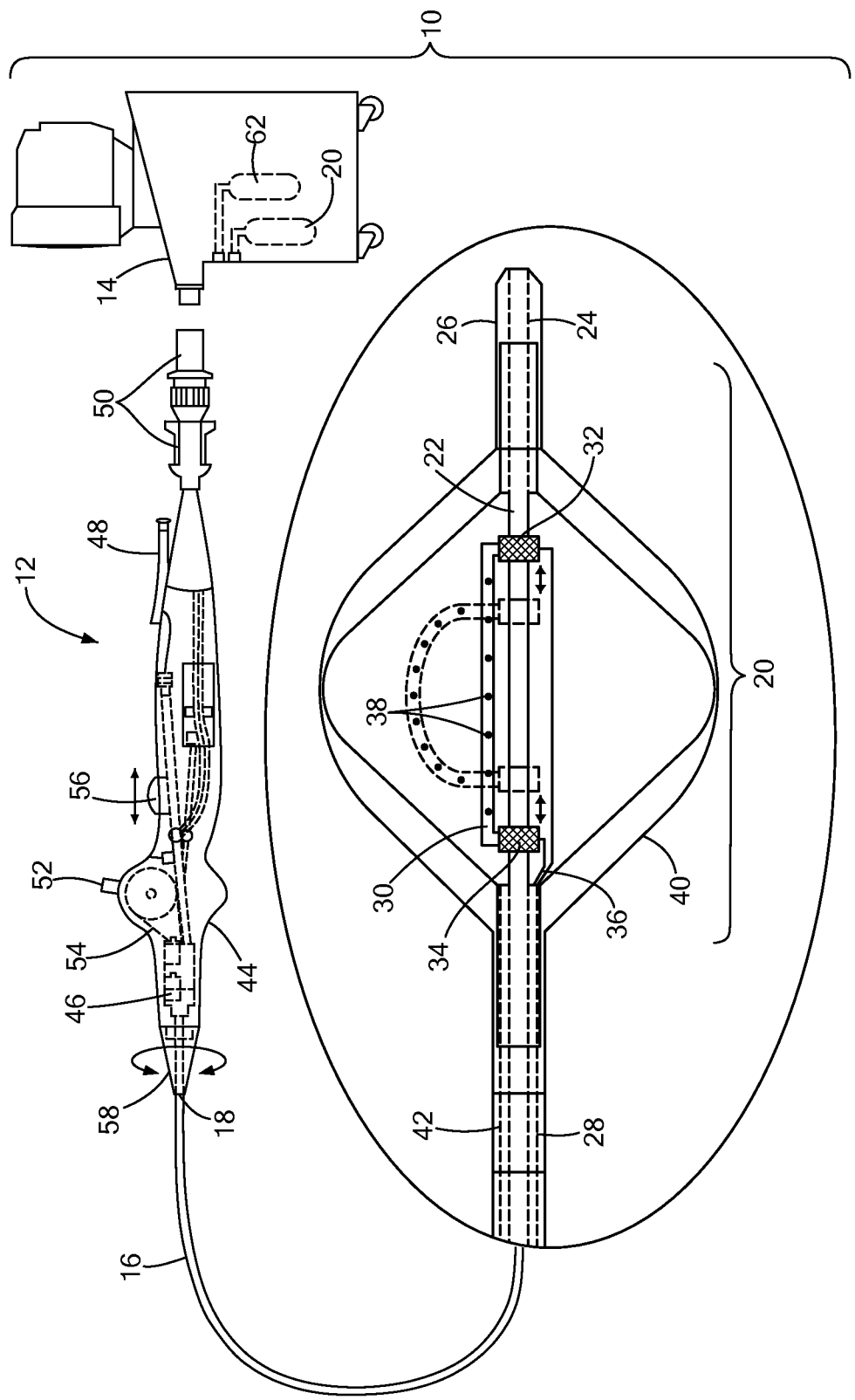
FIG. 1 is an illustration of an embodiment of a medical system constructed in accordance with the principles of the present invention.

The present invention advantageously provides a medical system and methods of use thereof in which the particular size, shape, and/or dimensions of the components of the system may be controlled and modified during use to provide ablative patterns or treatment delivery characteristics of various shapes and continuity, as well as having increased heat transfer efficiency during thermal exchange procedures. Referring now to the drawing figures in which like reference designations refer to like elements, an embodiment of a medical system constructed in accordance with principles of the present invention is shown in FIG. 1 and generally designated as "10." The system 10 generally includes a medical device 12 that may be coupled to a control unit 14 or operating console. The medical device 12 may generally include one or more treatment regions for energetic or other therapeutic interaction between the medical device 12 and a treatment site. The treatment region(s) may deliver, for example, cryogenic therapy, radiofrequency energy, or other energetic transfer with a tissue area in proximity to the treatment region(s), including cardiac tissue.

Figure 2:
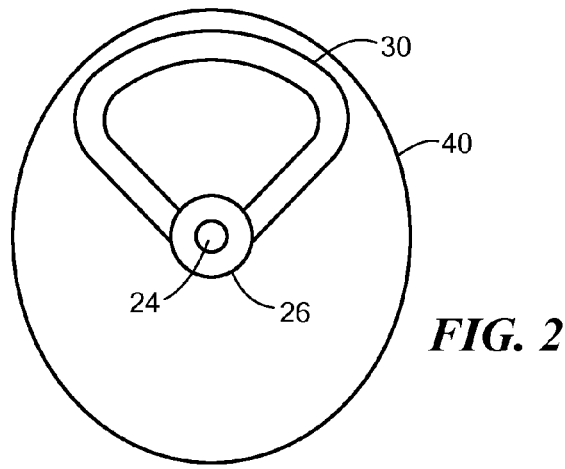
FIG. 2 is an illustration of a distal-to-proximal view of the medical device of the system of FIG. 1.

Now referring to FIGS. 1-2, the medical device 12 may include an elongate body 16 passable through a patient's vasculature and/or proximate to a tissue region for diagnosis or treatment, such as a catheter, sheath, or intravascular introducer. The elongate body 16 may define a proximal portion 18 and a distal portion 20, and may further include one or more lumens disposed within the elongate body 16 thereby providing mechanical, electrical, and/or fluid communication between the proximal portion of the elongate body 16 and the distal portion of the elongate body 16, as discussed in more detail below.

The medical device 12 may include a shaft 22 at least partially disposed within a portion of the elongate body 16. The shaft 22 may extend or otherwise protrude from a distal end of the elongate body 16, and may be movable with respect to the elongate body 16 in longitudinal and rotational directions. That is, the shaft 22 may be slidably and/or rotatably moveable with respect to the elongate body 16. The shaft 22 may further define a lumen 24 therein for the introduction and passage of a guide wire. The shaft 22 may include or otherwise be coupled to a distal tip 26 that defines an opening and passage therethrough for the guide wire.

The medical device 12 may further include a fluid delivery conduit 28 traversing at least a portion of the elongate body and towards the distal portion. The delivery conduit 28 may be coupled to or otherwise extend from the distal portion of the elongate body 16, and may further be coupled to the shaft 22 and/or distal tip of the medical device 12. The fluid delivery conduit 28 may be flexible, constructed from a shape memory material (such as Nitinol), and/or include other controllably deformable materials that allow the fluid delivery conduit 28 to be manipulated into a plurality of different geometric configurations, shapes, and/or dimensions. The fluid delivery conduit may further define a deflectable segment 30 at the distal portion of the device that can be controllably transitioned into a variety of different configurations. In particular, the deflectable segment 30 may include a distal end 32 and a proximal end 34 and a length therebetween. The proximal and/or distal ends of the deflectable segment 30 may be slidably and/or rotatably coupled to the elongate body 16, the shaft 22, and/or the distal tip 26 to allow the deflectable segment 30 to be configured into different configurations ranging from substantially linear (as shown in FIG. 1) to substantially helical or circumferential (as shown in FIG. 2), for example. Particular examples of combinations of the movable nature of the deflectable segment 30 of the fluid delivery conduit 28 may include 1) an anchored proximal end 34 with a slidable and/or rotatable distal end 32 with respect to the shaft 22 and/or distal tip 26; 2) an anchored distal end 32 and a slidable and/or rotatable proximal end 34 with respect to the shaft 22 and/or elongate body 16; or 3) both the proximal and distal ends are slidable and/or rotatable with respect to the shaft 22, elongate body 16 and/or distal tip 26. The controllable movement of the proximal and distal ends may be achieved or otherwise implemented through the use of one or more deflection control elements 36 coupled to the proximal and/or distal ends of the deflectable segment 30 and that further coupled to a proximal portion of the medical device accessible to an end user or physician. The deflection control elements 36 may include, for example, one or more steering wires, torque transmission structures, or other linkage engageable with the deflectable segment 30. The example in FIG. 1 illustrates the proximal and distal ends of the deflectable segment 30 being both rotatably and slidably coupled to the shaft. However, configurations where either the distal or proximal ends are securely anchored or fixed with respect to the shaft or elongate body while still allowing a desired degree of deflection, manipulation, and/or steering is also contemplated, as described herein.

Figure 3:
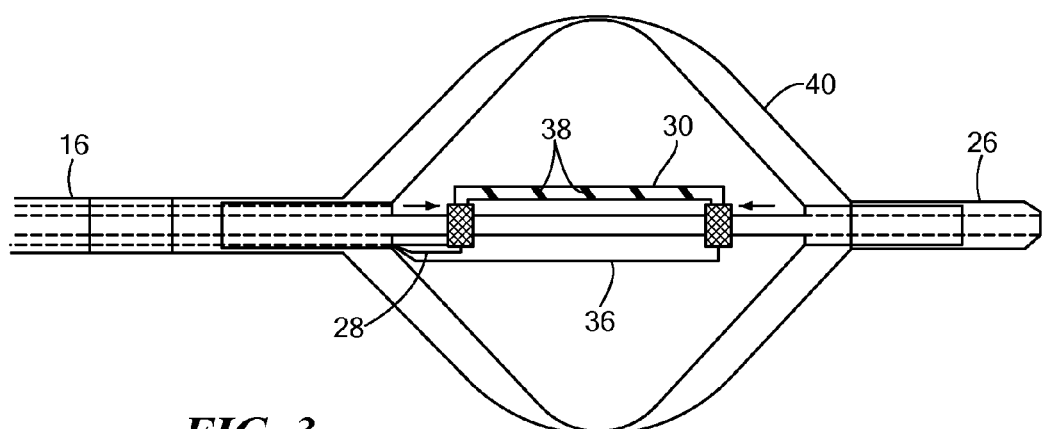
FIG. 3 is an illustration of an embodiment of a medical device constructed in accordance with the principles of the present invention.
Figure 4:
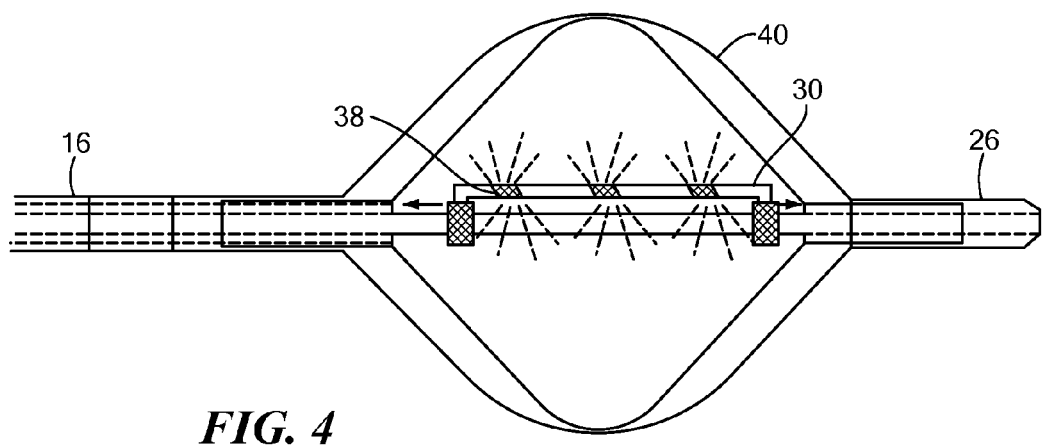
FIG. 4 is an additional illustration of the medical device of FIG. 3.

The fluid delivery conduit 28 may define a lumen therein for the passage or delivery of a fluid from the proximal portion of the elongate body 16 and/or the control unit 14 to the distal portion and/or treatment region of the medical device 12. The fluid delivery conduit 28 may further include one or more apertures or openings 38 therein, such as in the deflectable segment 30, to provide for the dispersion or directed ejection of fluid from the lumen to an environment exterior to the fluid delivery conduit 28. As shown in FIGS. 3 and 4, the openings 38 may be helically arranged around an outer circumference of the fluid delivery conduit, providing for a segment of the delivery conduit 28 that is extendable or collapsible to at least partially control the fluid dispersion. For example, when the portion of the fluid delivery conduit 28 containing the helical openings experiences a compressing force or manipulation, the size of the helical openings (e.g., the spacing between the walls of the fluid delivery conduit defining the helical openings) is controllably reduced or altogether eliminated, thus reducing or eliminating fluid flow out of the fluid delivery conduit. Oppositely, when the portion of the fluid delivery conduit 28 containing the helical openings experiences an extension or "stretching" force, the size of the helical openings (e.g., the spacing between the walls of the fluid delivery conduit defining the helical openings) is controllably increased, thus increasing fluid flow out of the fluid delivery conduit. The extension and compression of the fluid delivery tube 28 can be achieved through manipulation of one or more of the deflection control elements 36, as described herein.

Again referring to FIGS. 1 and 2, the medical device 12 may further include an expandable element 40 at the distal portion of the elongate body 16. The expandable element 40 may be coupled to a portion of the elongate body 16 and also coupled to a portion of the shaft 22 and/or distal tip 26 to contain a portion of the fluid delivery conduit 28 therein. The expandable element 40 defines an interior chamber or region that contains coolant or fluid dispersed from the fluid delivery conduit 28, and may be in fluid communication with an exhaust lumen 42 defined by or included in the elongate body 16 for the removal of dispersed coolant from the interior of the expandable element 40. The expandable element 40 may further include one or more material layers providing for puncture resistance, radiopacity, or the like.

The medical device 12 may include a handle 44 coupled to the proximal portion of the elongate body 16. The handle 44 can include circuitry for identification and/or use in controlling of the medical device 12 or another component of the system. For example, the handle 44 may include one or more pressure sensors 46 to monitor the fluid pressure within the medical device 12. Additionally, the handle 44 may be provided with a fitting 48 for receiving a guide wire that may be passed into the guide wire lumen 24. The handle 44 may also include connectors 50 that are matable directly to a fluid supply/exhaust and control unit 14 or indirectly by way of one or more umbilicals. The handle 44 may further include blood detection circuitry in fluid and/or optical communication with the injection, exhaust and/or interstitial lumens. The handle 44 may also include a pressure relief valve in fluid communication with the fluid delivery conduit 28 and/or exhaust lumen to automatically open under a predetermined threshold value in the event that value is exceeded.

The handle 44 may also include one or more actuation or control features that allow a user to control, deflect, steer, or otherwise manipulate a distal portion of the medical device from the proximal portion of the medical device. For example, the handle 44 may include one or more components such as a lever or knob 52 for manipulating the elongate body 16 and/or additional components of the medical device 12. For example, a pull wire 54 with a proximal end and a distal end may have its distal end anchored to the elongate body 16 at or near the distal portion, and/or may be coupled to the proximal or distal end of the deflectable segment 30 of the fluid delivery conduit 28. The proximal end of the pull wire 54 may be anchored to an element such as a cam in communication with and responsive to the lever 52. The medical device 12 may include an actuator element 56 that is movably coupled to the proximal portion of the elongate body 16 and/or the handle 44. The actuator element 56 may further be coupled to a proximal portion of the shaft 22 such that manipulating the actuator element 56 in a longitudinal direction causes the shaft 22 to slide towards either of the proximal or distal portions of the elongate body 16. The actuator element 56 may include a thumb-slide, a push-button, a rotating lever, or other mechanical structure for providing a movable coupling to the elongate body 16, the handle 44, and/or the shaft 22. Moreover, the actuator element 56 may be movably coupled to the handle 44 such that the actuator element is movable into individual, distinct positions, and is able to be releasably secured in any one of the distinct positions.

The medical device 12 may include one or more rotational control elements 58 that are rotatably coupled to the proximal portion of the elongate body 16 and/or the handle 44. The rotational control element(s) 58 may further be coupled to the proximal and/or distal ends of the deflectable segment 30 and/or the shaft such that rotating the rotational control element 58 about a longitudinal axis of the handle 44 and/or elongate body 16 results in similar rotation of the attached proximal and/or distal ends and/or the shaft at the distal portion of the medical device 12. The rotational control element 58 may include a knob, dial, or other mechanical structure for providing a rotatable coupling to the elongate body 16, the handle 44, and/or the shaft 22. Moreover, the rotational control element 58 may be rotatably coupled to the handle 44 and/or elongate body 16 such that the rotational control element is movable into individual, distinct positions, and is able to be releasably secured in any one of the distinct positions.

As the fluid delivery conduit 28 and the expandable element 40 may be coupled to the shaft 22 and/or distal tip, movement of the shaft 22 can allow the controllable transition of the fluid delivery conduit 28 and the expandable element 40 from one geometric shape, configuration, or dimension to another. By sliding and rotating the shaft 22 (in addition to and/or independently of the manipulation of the distal and/or proximal ends 32, 34 of the fluid delivery conduit 28), through manipulation of the actuator element 56 and/or rotational control element(s) 58 of the handle 44 for example, the fluid delivery conduit 28 can be manipulated into various geometries for the desired clinical or therapeutic effect. For example, the shaft 22 can be moved and rotated to transition the fluid delivery conduit 28 from a near linear configuration adjacent the shaft to a partial circumferential, looped configuration (i.e., a partial helical or spiral shape) about the shaft. The orientation of the looped configuration can further be modified by rotating the shaft 22 (and/or the proximal and distal ends of the deflection segment) through manipulation of the rotational control element(s) and the actuator element(s).

By using both rotational and longitudinal manipulation mechanisms of the medical device 12, the dimensions and geometry of the deflectable segment 30 of the fluid delivery conduit 28 can be increased and decreased as desired. For example, the fluid delivery conduit 28 may be manipulated through a range of diameters or curvilinear configurations such that a portion of the fluid delivery conduit 28 is adjacent a selected portion of the expandable element 40 for focused thermal exchange with a particular tissue region. On the other hand, a near-linear configuration of the fluid delivery conduit 28 can be selected to disperse fluid within the interior of the expandable element 40 for thermal exchange with tissue contacting an outer circumference of the expandable element 40. The linear configuration also facilitates ease of introduction and removal of the medical device 12 through the vasculature when the expandable element 40 is collapsed or evacuated (which may be further aided by the deflective, steering mechanisms described above).

The system 10 may further include one or more sensors to monitor the operating parameters throughout the system, including for example, pressure, temperature, flow rates, volume, or the like in the control unit 14 and/or the medical device 12, in addition to monitoring, recording or otherwise conveying measurements or conditions within the medical device 12 or the ambient environment at the distal portion of the medical device 12. The sensor(s) may be in communication with the control unit 14 for initiating or triggering one or more alerts or therapeutic delivery modifications during operation of the medical device 12. One or more valves, controllers, or the like may be in communication with the sensor(s) to provide for the controlled dispersion or circulation of fluid through the lumens/fluid paths of the medical device 12. Such valves, controllers, or the like may be located in a portion of the medical device 12 and/or in the control unit 14.

In an exemplary system, a fluid supply 60 including a coolant, cryogenic refrigerant, or the like, an exhaust or scavenging system (not shown) for recovering or venting expended fluid for re-use or disposal, as well as various control mechanisms for the medical system may be housed in the console. In addition to providing an exhaust function for the catheter fluid supply, the console may also include pumps, valves, controllers or the like to recover and/or re-circulate fluid delivered to the handle, the elongate body, and/or the fluid pathways of the medical device 12. A vacuum pump 62 in the control unit 14 may create a low-pressure environment in one or more conduits within the medical device 12 so that fluid is drawn into the conduit(s)/lumen(s) of the elongate body 16, away from the distal portion and towards the proximal portion of the elongate body 16. The control unit 14 may include one or more controllers, processors, and/or software modules containing instructions or algorithms to provide for the automated operation and performance of the features, sequences, or procedures described herein.

While the medical device 12 may be in fluid communication with a cryogenic fluid source to cryogenically treat selected tissue, it is also contemplated that the medical device 12 may alternatively or additionally include one or more electrically conductive portions or electrodes thereon coupled to a radio frequency generator or power source as a treatment or diagnostic mechanism.

Figure 5:
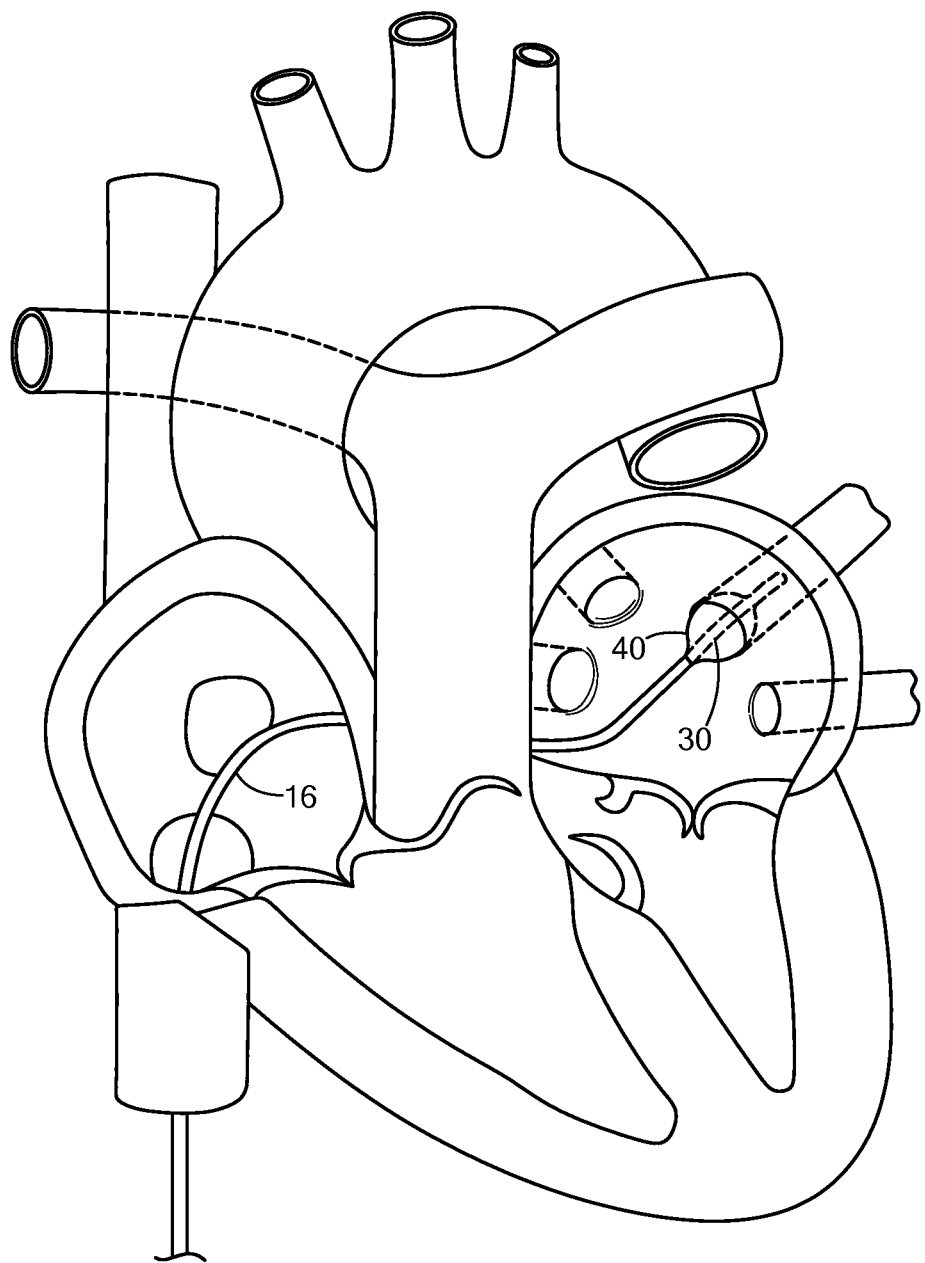
FIG. 5 is an illustration of an exemplary use of an embodiment of a medical system in accordance with the principles of the present invention.
Figure 6:
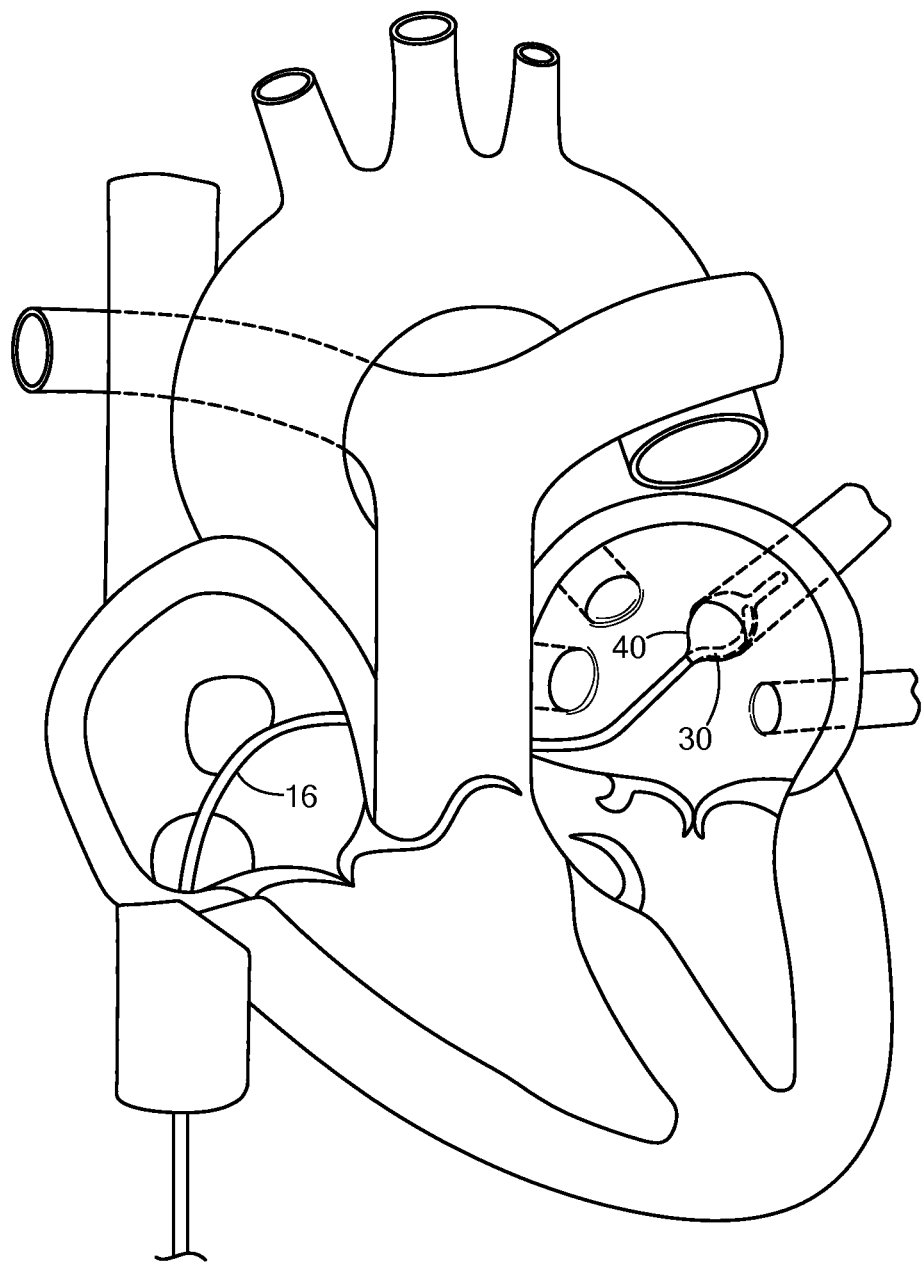
FIG. 6 is another illustration of an exemplary use of an embodiment of a medical system in accordance with the principles of the present invention

Now referring to FIGS. 5-6, in an exemplary method of use, the medical system 10 may be used to deliver therapeutic treatment to a targeted tissue area. For example, the medical device 12 may be positioned and operated to thermally treat or ablate a targeted tissue region in the heart, such as a pulmonary vein opening or ostia. The distal portion of the medical device 12 may be positioned adjacent the targeted tissue, with the deflectable segment 30 of the fluid delivery conduit 28 in a first geometric configuration, which may include a substantially linear configuration of the fluid delivery conduit adjacent the shaft 22, for example. Once the distal portion of the medical device has been positioned where desired with the deflectable segment 30 of the fluid delivery conduit in the selected configuration, it may be operated to thermally treat the tissue. For example, a cryogenic coolant or fluid may be circulated through the fluid delivery conduit 28 and into the interior of the expandable element 40 to expand the expandable element 40. The circulation of coolant within the expandable element 40 results in the reduced temperature of the expendable element and the tissue in proximity to it. Where the fluid delivery conduit includes helical slits or openings, the rate of coolant dispersion may be controlled at least in part by extending or compressing the fluid delivery conduit to modify the opening size (and thus coolant flow rate) out of the fluid delivery conduit and into the interior or chamber defined by the expandable element 40. The extent of the thermal exchange and/or realized temperatures of the expandable element 40 and thus the tissue may also be manipulated by one or more controls in the control unit 14 to provide for tissue ablation, mapping, or other therapeutic and/or diagnostic function. If the expandable element 40 is adjacent an opening or orifice of a blood vessel, such as a pulmonary vein, the balloon may be used to create a circular or circumferential treatment area or lesion on the thermally affected tissue.

Upon achieving the desired effect with the distal portion of the medical device 12 having the expandable element 40 and the deflectable segment 30 of the fluid delivery conduit in the first geometric configuration, the flow of coolant to the fluid delivery conduit 28 and thus the interior of the expandable element 40 38 may be discontinued. The distal portion of the medical device 12 may then be repositioned in proximity to a tissue region where additional thermal treatment may be performed. The fluid delivery conduit 28 may be configured into a second geometric configuration to create the desired therapeutic effect. For example, the deflectable segment 30 of the fluid delivery conduit may be transitioned into a curvilinear, arcuate, or helical shape. The deflected configuration of the fluid delivery tube may result in a portion of the deflectable segment 30 in close proximity to or immediately adjacent a portion of the expandable element 40. The transition may be achieved by manipulating the actuator element(s) 56 and/or the rotational control element(s) 58 as described above. Once the desired geometric configuration has been achieved, coolant may be re-introduced or otherwise circulated through the fluid delivery conduit 28 and into the interior of the expandable element 40.

Of note, as the fluid delivery conduit 28 is immediately adjacent an interior surface of the expandable element 40, which may be in contact with the targeted tissue site on the opposite side of the expandable element 40, there is a substantially reduced, if not altogether eliminated, extraneous thermal load or environment to interfere with the thermal exchange between the coolant exiting the fluid delivery conduit 28, the expandable element 40, and the adjacent tissue. In other words, the close proximity of the coolant dispersion from the fluid delivery conduit 28 towards the expandable element 40 combined with the close proximity of the tissue to the expandable element 40 reduces the heat loss from fluid flow around other portions of the exterior of the medical device 12. Moreover, because of the close proximity of the deflectable segment 30 to the expandable element 40 and the imparted shape change of the fluid delivery conduit, the resulting tissue region affected by the thermal transfer will substantially mimic or reflect the geometric shape of the deflectable segment 30, e.g., the treated area will be arcuate, curvilinear, or helical.

Accordingly, the second geometric configuration of the deflectable segment 30 may be used to impart a second tissue lesion and/or thermally affected area having a varied geometric pattern and/or dimension to that of the first tissue lesion or treatment area. The manipulation and/or repositioning of the distal portion of the medical device 12 and the deflectable segment 30 may be repeated as needed to achieve the desired therapeutic effect, which may include patterns of linear, curvilinear, arcuate, helical, and/or circumferential lesions or treatment areas.

The controllable geometric configuration of the distal portion of the medical device generally provides the ability to deliver therapeutic treatment in a variety of different geometric configurations, dimensions or shapes with a single device and further provides an ability to ensure continuity of an ablation lesion or pattern with a single device, rather than with several different devices. In addition, varying range of shapes and dimensions attainable with the manipulable fluid delivery conduit provides varying degrees of precision in treating tissue and/or creating an ablative lesion as a result of its respective geometric configurations, shapes, and/or dimensions. For example, a deployed, helical or circumferential configuration may be used during an initial stage of a procedure to treat a relatively large area of tissue, while a second linear or otherwise decreased profile may subsequently be used to treat smaller sections or specific areas of tissues within the broad region that require additional therapy. Although the exemplary use described above employed first and second geometric configurations, it is contemplated that a shaping element capable of more than two configurations may be employed and achieved through a combination of mechanical, thermal, and/or electrical forces, as well as through characteristics provided through material selection in the construction of the shaping element. Moreover, while examples and illustrations of particular geometric configurations have been provided, it is understood that virtually any shapes, configurations, and/or dimensions may be included and/or achieved by the medical device of the present invention, including but not limited to those shapes illustrated and described herein. A particular geometric configuration may include circular, conical, concave, convex, rounded, or flattened features and/or combinations thereof. Accordingly, an embodiment of the medical device of the present invention may be able to provide focal lesions, circular lesions, linear lesions, circumferential lesions, and combinations thereof.

It will be appreciated by persons skilled in the art that the present invention is not limited to what has been particularly shown and described herein above. In addition, unless mention was made above to the contrary, it should be noted that all of the accompanying drawings are not to scale. Of note, the system components have been represented where appropriate by conventional symbols in the drawings, showing only those specific details that are pertinent to understanding the embodiments of the present invention so as not to obscure the disclosure with details that will be readily apparent to those of ordinary skill in the art having the benefit of the description herein. Moreover, while certain embodiments or figures described herein may illustrate features not expressly indicated on other figures or embodiments, it is understood that the features and components of the system and devices disclosed herein are not necessarily exclusive of each other and may be included in a variety of different combinations or configurations without departing from the scope and spirit of the invention. A variety of modifications and variations are possible in light of the above teachings without departing from the scope and spirit of the invention, which is limited only by the following claims.

What is claimed is:

1. A method of thermally treating tissue, comprising:
   positioning an expandable element of a medical device adjacent to the tissue, the medical device includes a guide wire lumen at least partially disposed within the elongate body and at least partially disposed within the interior of the expandable element;
   delivering a fluid into an interior of the expandable element with a fluid delivery conduit to expand the expandable element, the fluid delivery conduit being in a first geometric configuration, the fluid delivery conduit including a deflectable segment defining a proximal end and a distal end with the proximal end being slidably and rotatably coupled to the guide wire lumen and the distal end being immovably fixed to the guide wire lumen;
   thermally treating a first region of the tissue with the expandable element;
   transitioning the fluid delivery conduit from the first geometric configuration into a second geometric configuration; and
   thermally treating a second region of the tissue with the expandable element.

2. The method according to claim 1, wherein the first region of tissue has a shape different from a shape of the second region of tissue.

3. The method according to claim 1, wherein the shape of the first region of tissue is substantially circular.

4. The method according to claim 1, wherein transitioning the fluid delivery conduit from the first geometric configuration into the second geometric configuration includes rotating at least a portion of the fluid delivery conduit about the guide wire lumen of the medical device.

5. The method according to claim 1, wherein transitioning the fluid delivery conduit from the first geometric configuration into the second geometric configuration includes longitudinally sliding at least a portion of the fluid delivery conduit along a guide wire lumen of the medical device.

6. The method according to claim 1, wherein delivering the fluid includes extending a portion of the fluid delivery conduit defining at least one opening that is helically arranged around an outer circumference of the fluid delivery conduit to increase a rate of fluid flow into the expandable element.

7. The method according to claim 1, wherein delivering the fluid includes compressing a portion of the fluid delivery conduit defining at least one opening that is helically arranged around an outer circumference of the fluid delivery conduit to decrease a rate of fluid flow into the expandable element.

8. The method according to claim 1, wherein thermally treating the tissue includes ablating at least a portion of the tissue, and the tissue includes an ostium of a pulmonary vein.

9. The method according to claim 1, wherein the first geometric configuration is substantially linear and the second geometric configuration is curvilinear.

10. The method according to claim 1, further comprising:
    terminating coolant dispersion into the interior cavity of the expandable element;
    transitioning the fluid delivery conduit from the second geometric configuration to the first configuration; and
    removing the expandable element from the tissue.

11. A method of thermally treating tissue, comprising:
    positioning an expandable element of a medical device adjacent to the tissue, the medical device including a guide wire lumen at least partially disposed within the expandable element;

delivering a fluid into an interior of the expandable element with a fluid delivery conduit to expand the expandable element, the fluid delivery conduit including a deflectable segment defining a proximal end and a distal end with the proximal end being slidably and rotatably coupled to the guide wire lumen and the distal end being immovably fixed to the guide wire lumen, the fluid delivery conduit being in a first geometric configuration;

thermally treating a first region of the tissue with the expandable element;

transitioning the fluid delivery conduit from the first geometric configuration into a second geometric configuration; and thermally treating a second region of the tissue with the expandable element.

12. The method of claim 11, wherein transitioning the fluid delivery conduit from the first geometric configuration into the second geometric configuration includes longitudinally sliding at least a portion of the fluid delivery conduit along the guide wire lumen of the medical device.

13. The method of claim 11, wherein the step of delivering the fluid includes extending a portion of the fluid delivery conduit defining at least one opening that is helically arranged around an outer circumference of the fluid delivery conduit to increase a rate of fluid flow into the expandable element.

14. The method of claim 11, wherein the step of delivering the fluid includes compressing a portion of the fluid delivery conduit defining at least one opening that is helically arranged around an outer circumference of the fluid delivery conduit to decrease a rate of fluid flow into the expandable element.

15. The method of claim 11, wherein thermally treating the tissue includes ablating at least a portion of the tissue, and the tissue includes an ostium of a pulmonary vein.

16. The method of claim 11, wherein the first geometric configuration is substantially linear and the second geometric configuration is curvilinear.

17. The method of claim 11, further comprising:
terminating coolant dispersion into the interior cavity of the expandable element;
transitioning the fluid delivery conduit from the second geometric configuration to the first configuration; and
removing the expandable element from the tissue.

18. A method of thermally treating tissue, comprising:
positioning an expandable element of a medical device adjacent to the tissue, the medical device including a guide wire lumen at least partially disposed within the expandable element;
delivering a fluid into an interior of the expandable element with a fluid delivery conduit to expand the expandable element, the fluid delivery conduit including a deflectable segment defining a proximal end and a distal end with the proximal end being slidably and rotatably coupled to the guide wire lumen and the distal end being immovably fixed to the guide wire lumen, the fluid delivery conduit further including at least one opening that is helically arranged around an outer circumference of the fluid delivery conduit, the fluid delivery conduit being in a first geometric configuration;
thermally treating a first region of the tissue with the expandable element;
transitioning the fluid delivery conduit from the first geometric configuration into a second geometric configuration; and
thermally treating a second region of the tissue with the expandable element.

* * * * *